United States Patent
Rodriguez

(10) Patent No.: US 6,310,054 B1
(45) Date of Patent: *Oct. 30, 2001

(54) PREVENTION OF OVARIAN CANCER BY ADMINISTRATION OF PROGESTIN PRODUCTS

(75) Inventor: Gustavo C. Rodriguez, Durham, NC (US)

(73) Assignee: New Life Pharmaceuticals Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/464,899

(22) Filed: Dec. 16, 1999

Related U.S. Application Data

(63) Continuation of application No. 08/713,834, filed on Sep. 13, 1996.

(51) Int. Cl.$^7$ ................................................ A61K 31/56
(52) U.S. Cl. .......................................... 514/179; 514/179
(58) Field of Search ............................................. 514/179

(56) References Cited

U.S. PATENT DOCUMENTS

| | | | |
|---|---|---|---|
| 3,608,075 | 9/1971 | Glen et al. | 424/238 |
| 3,957,982 | 5/1976 | Lachnit-Fixson et al. | 424/238 |
| 3,969,502 | 7/1976 | Lachnit-Fixson | 424/239 |
| 4,390,531 | 6/1983 | Edgren | 424/239 |
| 4,530,839 | 7/1985 | Pasquale | 514/171 |
| 4,544,554 | 10/1985 | Pasquale | 514/170 |
| 4,594,340 | 6/1986 | Partridge et al. | 514/167 |
| 4,616,006 | 10/1986 | Pasquale | 514/170 |
| 4,621,079 | 11/1986 | Lachnit-Fixson et al. | 514/170 |
| 4,628,051 | 12/1986 | Pasquale | 514/170 |
| 4,757,061 | 7/1988 | Faustini et al. | 514/177 |
| 4,760,053 | 7/1988 | Labrie | 514/15 |
| 4,780,497 | 10/1988 | Miller et al. | 514/414 |
| 4,800,198 | 1/1989 | DuLuca et al. | 514/167 |
| 4,808,578 | 2/1989 | Faustini et al. | 514/177 |
| 4,808,616 | 2/1989 | Buzzetti et al. | 514/177 |
| 4,814,327 | 3/1989 | Ottow et al. | 514/179 |
| 4,817,819 | 4/1989 | Kelly | 221/2 |
| 4,840,943 | 6/1989 | Buzzetti et al. | 514/177 |
| 4,870,069 | 9/1989 | Ottow et al. | 514/179 |
| 4,904,650 | 2/1990 | Buzzetti et al. | 514/177 |
| 4,921,843 | 5/1990 | Pasquale | 514/170 |
| 4,931,283 | 6/1990 | Tsuk | 424/449 |
| 4,933,184 | 6/1990 | Tsuk | 424/449 |
| 4,954,490 | 9/1990 | Barber | 332/164 |
| 4,962,098 | 10/1990 | Boissonneault | 514/170 |
| 5,006,518 | 4/1991 | Moguilewsky | 514/179 |
| 5,081,114 | 1/1992 | Gourvest et al. | 514/177 |
| 5,086,047 | 2/1992 | Gourvest et al. | 514/177 |
| 5,089,488 | 2/1992 | Ottow et al. | 514/179 |

(List continued on next page.)

FOREIGN PATENT DOCUMENTS

| | | |
|---|---|---|
| 0 253 607 A1 | 7/1987 | (EP) . |
| 0 253 607 B1 | 7/1987 | (EP) . |
| 0 628 312 A1 | 2/1994 | (EP) . |
| WO 95/26730 | 10/1995 | (WO) . |
| WO 98/10771 | 3/1998 | (WO) . |

OTHER PUBLICATIONS

Jordan et al., Cancer, 71(4, Suppl.), 1501–5 Abstract Only 1993.*

Allgood, V.E., et al., "Analysis Of Chicken Progesterone Receptor Function And Phosphorylation using An Adenovirus–Medicated Procedure For High–Efficiency DNA Transfer," *Biochemistry*, 36(1):224–232 (1997).

Arends, M.J. et al., "Apoptosis: Mechanisms And Roles In Pathology," *Int. Rev. Exp. Pathol.*, 32:223–254 (1991).

Arrick, B.A., et al., "Differential Regulation Of Three Transforming Growth Factor b Species In Human Breast Cancer Cell Lines By Estradiol," *Cancer Res.*, 50:299–303 (1990).

Bai, W. et al., "Differential Phosphorylation Of Chicken Progesterone Receptor In Hormone–Dependent And Ligand–Independent Activation," *J. Biol. Chem.*, 272(16):10457–10463 (1997).

Bates, R.C. et al. "Involvement Of Integrins In Cell Survival," *Cancer Metastasis Rev*, 14(3):191–203 (1995).

Berchuck, A. et al., "Regulation Of Growth Of Normal Ovarian Epithelial Cells And Ovarian Cancer Cell Lines By Transforming Growth, Factor–Beta," *Am. J. Obstet. Gynecol.*, 166:676–84 (1992).

Berchuck, A., et al., "The Role Of Peptide Growth Factors In Epithelial Ovarian Cancer," *Obstet. Gynecol*, 75:255–62 (1990).

Brenner, R.M. et al., "Cyclic Changes In The Primate Oviduct And Endometrium. In: *The Physiology Of Reproduction*," Knobil, E. et al., (eds.), New York: Raven Press, pp. 541–569 (1994).

Bu, S.Z. et al., "Progesterone Induces Apoptosis And Up–Regulation of p53 Expression In Human Ovarian Carcinoma Cell Lines," *Cancer*, 79:1944–1950 (1997).

Bundesverband der Pharmazeutishen Industrie, "Rote liste 1995," Ecv. Editio Cantor, *Aulendorf* (DE), pp. 75023–75024 (1995).

Chan, L.N. et al., "N–(4–Hydroxyphenyl) Retinamide Prevents Development Of Tlymphomas In AKR/J Mice," *Anticancer Research*, 17:499–503 (1997).

Cohen, J.J., "Apoptosis," *Immun. Today*, 14:126–130 (1993).

Delia, D. et al., "N–(4–hydroxyphenyl) Retinamide Induces Apoptosis Of Malignant Hemopoietic Cell Lines Including Those Unresponsive To Retinoic Acid," *Cancer Res.*, 53(24):6036–41 (1993).

(List continued on next page.)

*Primary Examiner*—Jerome D. Goldberg
(74) *Attorney, Agent, or Firm*—Raymond N. Nimrod

(57) ABSTRACT

The present invention relates to methods for preventing the development of epithelial ovarian cancer by administering progestin products, either alone or in combination with other agents such as estrogen products.

11 Claims, No Drawings

U.S. PATENT DOCUMENTS

| | | | |
|---|---|---|---|
| 5,108,995 | 4/1992 | Casper | 514/170 |
| 5,190,935 | 3/1993 | Binderup et al. | 514/167 |
| 5,206,229 | 4/1993 | Calverly et al. | 514/167 |
| 5,210,081 | 5/1993 | Reveendranath et al. | 514/179 |
| 5,227,375 | 7/1993 | Labrie et al. | 514/172 |
| 5,246,925 | 9/1993 | DuLuca et al. | 514/167 |
| 5,256,421 | 10/1993 | Casper | 424/449 |
| 5,262,408 | 11/1993 | Bergink | 514/182 |
| 5,278,155 | 1/1994 | Ikekawa et al. | 514/167 |
| 5,280,023 | 1/1994 | Ehrlich et al. | 514/177 |
| 5,288,717 | 2/1994 | Raveendranath et al. | 514/179 |
| 5,314,694 | 5/1994 | Gale et al. | 424/448 |
| 5,362,720 | 11/1994 | Labrie | 514/169 |
| 5,364,847 | 11/1994 | Labrie et al. | 514/182 |
| 5,373,004 | 12/1994 | DeLuca et al. | 514/167 |
| 5,374,629 | 12/1994 | Calverley et al. | 514/167 |
| 5,380,720 | 1/1995 | DeLuca et al. | 514/167 |
| 5,382,573 | 1/1995 | Casper | 514/170 |
| 5,387,582 | 2/1995 | Hansen | 514/167 |
| 5,389,622 | 2/1995 | Posner et al. | 514/167 |
| 5,401,731 | 3/1995 | Calverley et al. | 514/167 |
| 5,411,949 | 5/1995 | Neef et al. | 514/167 |
| 5,418,228 | 5/1995 | Bennick | 514/182 |
| 5,422,119 | 6/1995 | Casper | 424/449 |
| 5,428,029 | 6/1995 | Doran et al. | 514/167 |
| 5,434,146 | 7/1995 | Labrie et al. | 514/169 |
| 5,446,035 | 8/1995 | Neef et al. | 514/167 |
| 5,451,574 | 9/1995 | Baggiolini et al. | 514/167 |
| 5,461,041 | 10/1995 | Bergink et al. | 514/178 |
| 5,468,736 | 11/1995 | Hodgen | 514/179 |
| 5,484,782 | 1/1996 | DeLuca et al. | 514/167 |
| 5,486,511 | 1/1996 | Weintraub et al. | 514/178 |
| 5,496,813 | 3/1996 | Eugster et al. | 514/172 |
| 5,502,044 | 3/1996 | Buzzetti et al. | 514/177 |
| 5,512,554 | 4/1996 | Baggiolini et al. | 514/167 |
| 5,532,228 | 7/1996 | Neef et al. | 514/167 |
| 5,536,713 | 7/1996 | DuLuca et al. | 514/167 |
| 5,547,947 | 8/1996 | Dore et al. | 514/167 |
| 5,554,599 | 9/1996 | GrueSorenen et al. | 514/167 |
| 5,595,970 | 1/1997 | Garfield et al. | 514/12 |
| 5,620,705 | 4/1997 | Dong et al. | 424/472 |
| 5,633,011 | 5/1997 | Dong et al. | 424/451 |
| 5,741,786 | 4/1998 | Hamersma et al. | 514/173 |
| 5,747,480 | 5/1998 | Gast | 514/179 |
| 5,770,227 | 6/1998 | Dong et al. | 424/480 |
| 5,783,208 | 7/1998 | Yenkateshwaran et al. | 424/448 |
| 5,811,416 | 9/1998 | Chwalisz et al. | 514/177 |
| 5,827,876 | 10/1998 | Sabatucci | 514/448 |
| 5,855,906 | 1/1999 | McClay | 424/433 |
| 5,858,405 | 1/1999 | Gast | 424/464 |
| 5,876,746 | 3/1999 | Jona et al. | 424/449 |
| 5,880,137 | 3/1999 | Miller et al. | 514/323 |
| 5,888,543 | 3/1999 | Gast | 424/464 |
| 5,891,868 | 4/1999 | Cummings et al. | 514/178 |
| 5,898,038 | 4/1999 | Yallampalli et al. | 514/742 |
| 5,922,349 | 7/1999 | Elliesen et al. | 424/449 |
| 5,922,542 | 7/1999 | Ralston et al. | 435/6 |
| 5,948,775 | 9/1999 | Koko et al. | 514/212 |
| 5,962,444 | 10/1999 | Cook et al. | 514/177 |
| 5,972,377 | 10/1999 | Jona et al. | 424/449 |
| 5,985,910 | 11/1999 | Miller et al. | 514/415 |
| 5,994,337 | 11/1999 | Washburn et al. | 514/182 |
| 5,998,137 | 12/1999 | Grainter et al. | 435/6 |
| 6,001,846 | 12/1999 | Edwards et al. | 514/285 |
| 6,015,805 | 1/2000 | Cook et al. | 514/176 |
| 6,020,328 | 2/2000 | Cook et al. | 514/176 |
| 6,028,064 | 2/2000 | Rodriguez | 514/177 |
| 6,034,074 | 3/2000 | Rodriguez et al. | 514/167 |

OTHER PUBLICATIONS

Eguchi, Y. et al., "Isolation And Characterization Of The Chicken bcl–2 Gene: Expression In A Variety Of Tissues Including Lymphoid And Neuronal Organs In Adult And Embryo," *Nucleic Acids Research*, 20(16):4187–4192 (1992).

el–Bayoumy, K. et al., "Chemo Prevention Of Cancer By Organoselenium Compounds," *J. Cell. Biochem, Suppl.*, 22:92–100 (1995).

Ellis, R. et al., "Mechanisms of Cell Death," *Ann. Rev. Cell. Bio.*, 17:663–698 (1991).

Evans, D.L. et al., "Molecular Evolution And Secondary Structural Conservation In The B–Cell Lymphoma Leukemia 2 (bcl–2) family Of Proto–Oncogene Products," *J. Mol. Evol.*, 41(6):775–83 (1995).

Fredrickson, T.N. et al., "Ovarian Tumors Of The Hen," *Environ Health Perspect*, 73:35–44 (1987).

Gentry, L.E. et al., "Type I Transforming Growth Factor–Beta: Amplified Expression And Secretion Of Mature And Precursor Polypeptides In Chinese Hamster Ovary Cells," *Mol. Cell. Biol.*, 7:3418–27 (1987).

Grimes et al., "Primary Prevention Of Gynecologic Cancers," *Am. J. Obstetrics And Gynecology*, 172(1):227–235 (1995).

Havrilesky, L.J., et al., "Regulation Of Apoptosis In Normal And Malignant Ovarian Epithelial Cells By Transforming Growth Factor–Beta," *Cancer Research*, 55:944–948 (Feb. 15, 1995).

Hickey, M.J., et al., "Metabolic And Endocrinologic Effects Of Steroidal Contraception Obstetrics," Ch. 24, J. Sciarra, Editor, 1996 revised edition, Lippincott, Philadelphia, pp. 1–14 (1996).

Hotchkiss, J. et al., "The Menstrual Cycle And Its Neuroendocrine Control," In: *The Physiology Of Reproduction*, Knobil, E. et al. (eds.), New York: Raven Press, pp. 711–736 (1994).

Hurteau, J.A., et al., "Transforming Growth Factor–Beta Inhibits Proliferation Of Human Ovarian Cancer cells Obtained From Ascites," *Cancer*, 74:93–99 (1994).

Johnson, A.J. et al., "Expression of bcl–2 And nr–13 In Hen Ovarian Follicles During Development," *Biol. Repro.*, 57:1096–1103 (1997).

Kaiserman–Abramof, I. et al., "Ultrastructural Epithelial Conation Of The Primate Endometrium (Rhesus Monkey," *Am J. Anat.*, pp. 13–30 (1989).

Lingeman, C.H., "Etiology Of Cancer Of The Human Ovary," A Review, *J. Natl. Cancer Inst.*, 53:1603–1618 (1974).

Lotan, R., "Retinoids In Cancer Chemo Prevention," [Review] *FASEB J.*, 10(9): 1031–1039, (1996).

Lumbiganon, P., "Depot–Medroxyprogesterone Acetate (DMPA) And Cancer Of The Endometrium And Ovary," *Contraception*, 49:203–209 (Mar., 1994).

Mulheron, G.W., et al., "Rat Thecal/Interstitial Cells Express Transforming Growth Factor–Beta Type 1 and 2 Is Regulated By Gonadotropin In Vitro," *Endocrin*, 129:368–373 (1991).

Mulheron, G.W., et al., "Rat Granulosa Cells Express Transforming Growth Factor–Beta Type 2 Messenger Ribonucleic Acid Which Is Regulatable By Fillide Stimulating Hormone In Vitro," *Endocrin*, 126:1777–1779 (1990).

Mutch, D.G., et al., "Biology Of Epithelial Ovarian Cancer," *Clin. Obstet. Gynecol.*, 37:406–422 (1994).

O'Brien, V. et al., "Expression Of The Integrin Alpha 5 Subunit In HT29 Colon Carcinoma Cells Suppresses Apoptosis Triggered By Serum Deprivation," *Ex. Cell. Res.*, 224(1):208–213 (1996).

Oberhammer, F.A., et al., "Induction Of Apoptosis In Cultured Hepatocytes And In Regressing Liver By Transforming Growth Factor–Beta 1," *Proc. Natl. Acad. Sci. USA*, 89:5408–5412 (1992).

Oridate N. et al., "Inhibition Of Proliferation And Injunction Of Apoptosis In Cervical Carcinoma Cells By Retinoids: Implications For Chemo Prevention," *J. Cell. Biochem.*, Suppl, 23:80–86 (1995).

Pasquele, R.M., et al., "Chemoprevention By S–Adenosyl–L–Methionine Of Rat Liver Carcinogenesis Initiated by 1,2–dimethylhydrazine And Promosted By Orotic Acid," *Carcinogenesis* 16(2):427–30 (1995).

Pfleiderer, "di Problematik einer prophylaktischen Chemotherapie, einer der Remission bei der Therapie des Ovarialkarzinoms," *Gerburstsh u. Frauenheilk*, 36(2):132–139 (1976).

Physician's Desk Reference 1996, Product Information, pp. 1871–1876, 2135–2138, 2601–2604, 2759–2762, and 2813–2818 (1996).

Ponzoni, M. et al., "Differential Effects Of N–(4–hydroxyphenyl) Retinamide And Retinoic Acid On Neuroblastoma Cells: Apoptosis Versus Differentiation," *Can. Res.*, 55(4):853–61 (1995).

Qin, S., et al., "Cooperation Of Tyrosine Kinases p72syk and p53/561yn Regulates Calcium Mobilization In Chicken B Cell Oxidant Stress Signaling," *Eur. J. Biochem*, 236(2):443–9 (1996).

Rampalli, A.M., et al., "Insulin Regulates Expression Of c–fos And c–jun and Suppresses Apoptosis Of Lens Epithelial Cells," *Cell. Growth Differ.*, 6(8):945–53 (1995).

Reddy, B.S., et al., "Chemo Prevention Of Colon Carcinogenesis By Dietary Perillyl Alcohol," *Cancer Res.*, 57(3):420–5 (1997).

Roberts, A.B., et al. "Mechanistic Interrelationships Between Two Superfamilies: The Steroid Retinoid Receptors And Transforming Growth Factor–Beta," In: Cancer Surveys, vol. 14: Growth Regulation By Nuclear Hormone Receptors, *Imperial Cancer Research Fund*, pp. 205–217 (1992).

Rodriquez, G.C., et al., "Epidermal Growth Factor Receptor Expression In Normal Ovarian Epithelium And Ovarian Cancer. II. Relationship Between Receptor Expression And Response To Epidermal Growth Factor," *Am. J. Obstet. Gynecol.*, 164: 745–750 (1991).

Rotello, R.J., et al., "Coordinated Regulation Of Apoptosis And Cell Proliferation By Transforming Growth Factor–Beta 1 In Cultured Uterine Epithelial Cells," *Proc. Natl. Acad. Sci. USA*, 88:3412–3415 (1991).

Rudel, H.W., "Pharmacology Of Contraceptive Steroids," Chapter 19, In: Gynecology and Obstetrics J. Sciarra, Editor, 1996 revised edition, Lippincott, Philadelphia, pp. 3–6 (1996).

Sankaranarayanan, R., et al., "Retinoids As Cancer–Preventive Agents," [Review] *IARC Sci. Publ.*, (139):47–59 (1996).

Schildkraut, J.M. et al., "Relationship Between Lifetime Ovulatory Cycles And Overexpression Of Mutant p53 In Epithelial Ovarian Cancer," *J. National Cancer Institute*, 89(13):932–938 (Jul. 2, 1997).

Scott, J.S., "How To Induce Ovarian Cancer: And How Not To," *British Medical J.*, 289:781–784 (Sep. 29, 1984).

Seewaldt, V.L. et al., "All–Trans–Retinoic Acid Mediates GI Arrest But Not Apoptosis Of Normal Human Mammary Epithelial Cells," *Cell Growth Differ.*, 6(7):631–41 (1995).

Syvala, H. et al., "Expression Of The Chicken Progesterone Receptor Forms A And B Is Differentially Regulated By Estrogen In Vivo," *Biochemical and Biophysical Research Communications*, 231:573–576 (1997).

Taetle, R., et al., "Effects Of Transforming Growth Factor–Beta 1 On Growth And Apoptosis Of Human Acute Myelogenous Leukemia Cells," *Cancer Research*, 53:3386–3393 (1993).

Takayama, S. et al., "Evolutionary Conservation Of Function Among Mammalian, Avian, And Viral Homologs Of The bcl–2 Oncoprotein," *DNA Cell. Biol.* 13(7):678–92 (1994).

Thompson, H.J. et al., "Sulfone Metabolite Of Sulindac; Inhibits Mammary Carcinogenesis," *Cancer Res.*, 57(2):267–71 (1997).

Thompson, H.J. et al., "Ip C. Comparison Of The Effects Of An Organic And Inorganic Form Of Selenium On A Mammary Carcinoma Cell Line," *Carcinogenesis* 15(2):183–6 (1994).

Toma, S. et al., "Effects of Al–Trans–Retinoic Acid And 13–Cis–Retinoic Acid On Breast–Cancer Cell Lines: Growth Inhibition And Apoptosis Induction," *Int. J. Cancer*, 70(5):619–27 (1997).

Vilgrasa, X. et al., "Differential Expression of bcl–2 and bcl–x During Chicken Spermatogenesis," *Mol. Reprod. Dev.*, 47(1):26–9 (1997).

Wakefield, L. et al., "Regulation Of Transforming Growth Factor–Beta Subtypes By Members Of The Steroid Hormone Superfamily," *J. Cell. Sci. Suppl.* 13:139–148 (1990).

Wijsman, J.H. et al., "A New Method To Detect Apoptosis In Paraffin Sections: In Situ End–Labeling Of Fragmented DNA," *J. Histochem. Cytochem.*, 41:7–12 (1993).

Woolveridge, I., et at., "The Inhibition Of Androstenedione Production In Mature Thecal Cells From The Ovary Of The Domestic Hen (*Gallus domesticus*): Evidence For The Involvement Of Progestins," *Steroids*, 62:214–220 (1997).

Yanagihara, K. et al., "Transforming Growth Factor–Beta 1 Induces Apoptotic Cell Death In Cultured Human Gastric Carcinoma Cells," *Cancer Res.*, 52:4042–4045 (1992).

Dolivet et al., "Current Knowledge On The Action Of Retinoids In Carcinoma Of The Head And Neck," [Review], *Rev. Laryngol. Otol. Rhinol. (Bord)* 117(1):19–26 (1996) (English abstract).

Etches et al., "Reptilian And Avian Follicular Hierarchies: Models For The Study Of Ovarian Development," *J. Exp. Zoo.*, Suppl. 4:112–122 (1990).

Fukuda et al., "Induction Of Apoptosis By Transforming Growth Factor–1 In The Rat Hepatoma Cell Fine McA–RH7777: A Possible Associate With Tissue Transglutaminase Expression," *Hepatology*, 18:945–953 (1993).

Gould, "Cancer Chemoprevention And Therapy By Monoterpenes," *Environ. Health Perspect.*, 105 (Suppl 4):977–9 (1997).

Kuo, "Antiproliferative Potency Of Sturcturally Distinct Dietary Flavonoids On Human Colon Cancer Cells," *Cancer Lett.*, 110(1–2):41–8 (1996).

Mayr et al., "Sequence Of An Exon Of Tumour Suppressor p53 Gene—A Comparative Study In Domestic Animals: Mutation In A Feline Comparative Study In Domestic Animals; Mutation In A Feline Solid Mammary Carcinoma," *Br. Vet. J.*, 151(3):325–9 (1995).

Wilson "Adeno–Carcinomata In Hens Kept In A Constant Environment," *Poult. Sci.*, 37:1253 (1958).

Milligan et al., "Programmed Cell Death During Development Of Animals," *Cellular Aging and Cell Death*: Wiley–Liss Inc., Holbrook, et al., (Eds), pp. 181–208 (1996).

Canman et al., "DNA Damage Responses: P–53 Induction, Cell Cycle Pertubations, And Apoptosis," *Cold Spring Harbor Symp. Quant. Biol.*, 59:277–286 (1994).

Baker et al., "Etiology, Biology, And Epidemiology Of Ovarian Cancer," *Seminars in Surgical Oncology* 10:242–248 (1994).

Amos et al., "Genetic Epidemiology Of Epithelial Ovarian Cancer," *Cancer* 71:566–72 (1993).

Wittemore, Characteristics Relating To Ovarian Cancer Risk: Implications For Preventing And Detection, Gynecologic Oncology 55: S15–S19, 1994.

Greene et al., "The Epidemiology Of Ovarian Cancer," *Seminars in Oncology*, 11:209–225 (1984).

Wittemore et al., "Characteristics Relating To Ovarian Cancer Risk: Collaborative Analysis Of 12 US Case–Control Studies," *Am. J. Epidem.* 136:1212–1220 (1992).

Wu et al., "Personal And Environmental Characteristics Related To Epithelial Ovarian Cancer," *Am. J. Epidem.*, 108(6): 1216–1227 (1988).

Rossing et al., "Ovarian Tumors In A Cohort Of Infertile Women," *New Engl. J. Med.*, 331:771–776 (1994).

Casagrande et al., "Incessant Ovulation" and "Ovarian Cancer," *Lancet* at pp. 170–172 (Jul. 28, 1979).

Rosenberg et al., (*The WHO Collaborative Study Of Neoplasia And SteroiD Contraceptives*)"A Case Control Study Of Oral Contraceptive Use and Invasive Epithelial Ovarian Cancer," *Am. J. Epidem.*, 139:654–661 (1994).

Stanford et al., "Epithelial Ovarian Cancer And Combined Oral Contraceptives," *Int'l J. Epidem.*, 18:538–545 (1989).

Lee et al., "The Reduction In Risk Of Ovarian Cancer Associated With Oral Contraceptive Use," *New Engl. J. Med.*, 316:650–655 (1987).

Gross et al., "The Estimated Effect Of Oral Contraceptive Use On The Cumulative Risk Of Epithelial Ovarian Cancer," *Obstetrics Gynecology*, 83:419–24 (1994).

Franseschi et al., "Pooled Analysis Of 3 European Case–Control Studies Of Epithelial Ovarian Cancer: III. Oral Contraceptive Use," *Int'l J. Cancer*, 49:61–65 (1991).

Rosenblatt et al., "High–Dose And Low–Dose Combined Oral Contraceptives: Protection Against Epithelial Ovarian Cancer and The Length Of The Protective Effect," *Eur. J. Cancer*, 28A:1872–76, 1992.

Stanford et al., (*The WHO Collaborative Study Of Neoplasia And Steroid*), "Depot–Medroxyprogesterone Acetate (DMPA) And Risk Of Epithelial Ovarian Cancer," *Int'l J. Cancer*, 49:191–195 (1991).

Liang et al., "Risk Of Breast, Uterine Corpus, And Ovarian Cancer In Women Receiving Medroxyprogesterone Injections," *JAMA*, 249:2909–2912 (1983).

Lowe et al., "P53–Dependent Apoptosis in Tumor Progression And In Cancer Therapy," *Cellular Aging And Cell Death*: Wiley–Liss Inc., Holbrook et al., (Eds.), pp. 209–234 (1996).

Lockshin et al., "The Biology of Cell Death and Its Relationship to Aging" *Cellular Aging and Cell Death*, Wiley–Liss Inc., Holbrook et al., (Eds.), pp. 167–180 (1996).

Bast et al., "Ovarian Cancer," Harrison's Principles Of Internal Medicine, Thirteenth Edition, Isselbacher et al., (Eds.), McGraw–Hill, New York, Chapter 321, pp. 1853–1858 (1994).

Rodriquez et al., "Estrogen Replacmenet Therapy And Fatal Ovarian Cancer," *Am. J. Epidem.*, 141:828–835 (1995).

Dunn, I.C., et al., "The Effect of Photoperiodic History On Egg Laying In Dwarf Broiler Hens," In: Physiology And Reproduction on: *Poultry Science*, vol. 71, pp. 2090–2098 (1992).

Christopherson, W.A. et al., "Responsiveness Of Human Carcinoma Cells Of Gynecologic Origin To 1,25–Dihydroxycholecalciferol," *Am. J. Obstet. Gynecol.*, 155(6):1293–1296 (1986).

Moore, T.B., et al., "Differentiating Effects of 1,25–Dihydroxycholecalciferol (D3) on La–N–5 Human Neuroblastoma Cells And Its Synergy With Retinoic Acid," *Journal Of Petriatric Hematology/Oncology*, 17(4):311–317 (Nov., 1995).

Rustin, G.J.S. et al., "Trial Of Isotretinoin And Calcitriol Monitored By CA 125 In Patients With Ovarian Cancer," *British Journal Of Cancer*, 74(9):1479–1481 (1996).

Saunders, D.E., et al., Repression Of c–myc Expression In Ovarian Carcinoma Cells by 1,25–Dihydroxyvitamin D3, *Twenty–Third Annual Meeting Of The Society Of Gynecologic Oncologiest*, Mar. 15–18, 1992. *Gynecol. Oncol.*, 45(1):83–84 (1992) (Abstract).

Saunders, D.E. et al., "Receptors for 1,25–Dihydroxyvitamin D3 in Gynecologic Neoplasms," *Gynecologic Oncology*, 44(2):131–136 (1992).

Saunders, D.E. et al., "Nonreproductive Hormones As Biologic Modifiers In Ovarian Carcinomas," *Twenty–Fourth Annual Meeting Of The Society Of Gynecologic Oncologiest*, Feb. 7–10, 1993. *Gynecol. Oncol*, 49(1):118 (1993) (Abstract).

Saunders, D.E. et al., "Inhibition Of c–myc In Breast And Ovarian Carcinoma Cells By 1,25–Dihydroxyvitamin D3, Retinoic Acid And Dexamethasone," *Anti–Cancer Drugs*, 4(2):201–208 (1993).

Saunders, D.E. et al., "Inhibition Of Breast And Ovarian Carcinoma Cell Growth By 1,25–Dihydroxyvitamin D3, Combined With Retonic Acid Or Dexamethasone," *Anti–Cancer Drugs*, 6(4):562–569 (1995).

Corder, E.H., et al., "Vitamin D And Prostate Cancer: A Prediagnostic Study With Stored Sera," *Cancer Epidemiology, Biomarkers & Prevention*, 2:467–472 (1993).

Santiso–Mere et al., "Positive Regulation Of The Vitamin D Receptor By Its Cognate Ligand In Heterolngous Expression Systems," *Molecular Endocrinology*, 7(7):833–839 (1993).

Davoodi et al., "Modulation Of Vitamin D Receptor And Estrogen Receptor By 1,25 (OH)2–Vitamin D3 In T–47D Human Breast Cancer Cells," *J. Steroid Biochem. Molec. Biol.*, 54(3/4):147–153 (1995).

Colston et al., "1–25–Dihydroxyvitamin D3 And Malignant Melanoma: The Presence Of Receptors And Inhibition Of Cell Growth In Culture," *Endocrinology*, 108:1083–1086 (1981).

Sato et al., "Antitumor Effect of 1a–Hydroxyvitamin D3," *Tohoku J. Exp. Med.*, 138:445–446 (1982).

Eisman et al., "Suppression Of In Vivo Growth Of Human Cancer Solid Tumor Xenografts By 1,25–Dihydroxyvitamin D3," *Cancer Research*, 47:21–25 (1987).

Dokoh et al., "Influence of 1,25–Dihydroxyvitamin D3 on Cultured Osteogenic Sarcoma Cells: Correlation With The 1,25–Dihydroxyvitamin D3 Receptor," *Cancer Research*, 44:2103–2109 (1984).

Mangelsdorf et al., "1,25–Dihydroxyvitamin D3–induced Defferentiation In A Human Promyelocytic Leukemia Cell Line (HL–60): Receptor Mediated Maturation To Macrophage–Like Cells," *J. Cell. Biol.*, 98:391–398 (1984).

Chida et al., "Inhibition Of Tumor In Mouse Skin By 1a, 25–Dihydroxyvitamin D31," *Cancer Research*, 45:5426–5430 (1985).

Oikawa et al., Antitumor Effect Of 22–oxa–1a–Dihydroxyvitamin D3, A Potent Angiogenesis Inhibitor, On Rat Mammary Tumors Induced By 7,12–Dimethylbenz[a]anthracene, *Anti–Cancer Drugs*, 2:475–480 (1991).

Frampton et al., "Inhibition Of Human Cancer Cell Growth By 1,25–Dihydroxyvitamin D3 Metabolites1," *Cancer Research*, 43:4443–4447 (1983).

Sporn, M.B. et al., "Prevention Of Carciogenesis With Vitamin D Analogs," *Proceedings American Association For Cancer Research*, No. 34, Abstracts 622 (Mar., 1993).

Saunders et al., "Additive Inhibition of RL95–2 Endometrial Carcinoma Cell Growth By Carboplatin and 1,25–Dihydroxyvitamin D3," *Gynecologic Oncology*, 51:155–159 (1993).

Welsh, J., "Induction Of Apoptosis In Breast Cancer Cells In Response To Vitamin D And Antiestrogens," *Biochem. Cell. Biol.*, 72:537–545 (1994).

Narvaez et al., "Characterization Of A Vitamin D3–Resistant MCF–7 Cell Line," *Endocrinology*, 137(2):400–409 (1996).

Lefkowitz et al., "Sunlight, Vitamin D, And Ovarian Cancer Mortality Rates In U.S. Women," *International Journal Of Epidemiology*, 23(6):1133–1136 (1994).

Studzinski et al., "Sunlight–Can It Prevent As Well As Cause Cancer?" *Cancer Research*, 55:4014–4022 (1995).

Speroff et al., "Steroid Contraception," *Clinical Gynecologic Endocrinology And Infirtility*, Chapter 15, Fourth Edition, pp. 461–498 (1989).

Hammond, "Climateric," *Danforth's Obstetrics And Gynecology*, Chapter 42, Seventh Edition, pp. 771–790 (1994).

Young, "Gynecologic Malignancies, Ovarian Cancer," *Harrison's Principles Of Internal Medicine*, Thirteenth Edition, pp. 1605–608 (1994).

Ravin, L.J. et al., *Remington's Pharmaceutical Sciences*, 18th Ed., Chpts., 75–92 (1990, Mack Publishing Co., Easton, PA 18042).

Wingo, P.A. et al., "Cancer Statistics, 1995," *CA Cancer Journal For Clinicians (A Journal Of The American Cancer Society)*, 45(1):30 (1995).

Dodd, R.C. et al., "Vitamin D Metabolites Change The Phenotype Of Monoblastic U937 Cells," *Proc. Natl. Acad. Sci., USA*, 80:7538–7541 (Dec., 1983).

Gao, Y. et al., "The Effects Of Chemotherapy Including Cisplatin On Vitamin D Metabolism," *Endocrine Journal*, 40(6):737–742 (1993).

Grimes et al., "Primary Prevention Of Gynecologic Cancers," Am. J. Obstetrics And Gynecology, 172(1):227–235 (1995).

Rosenberg et al., (The WHO Collaborative Study Of Neoplasia And Steroid Contraceptives) "A Case Control DStudy Of Oral Contraceptive Use And Invasive Epithelial Overian Cancer," Am. J. Epidem, 139:654–661 (1994).

\* cited by examiner

PREVENTION OF OVARIAN CANCER BY ADMINISTRATION OF PROGESTIN PRODUCTS

This is a continuation of application Ser. No. 08/713,834, filed on Sep. 13, 1996.

FIELD OF THE INVENTION

The present invention relates generally to methods of preventing the development of ovarian cancer by administering progestin products, alone or in association with other hormones such as estrogen products.

BACKGROUND OF THE INVENTION

Ovarian cancer is the fourth leading cause of cancer deaths among women in the United States and causes more deaths than all other gynecologic malignancies combined. In the United States, a woman's lifetime risk of developing ovarian cancer is 1 in 70. In 1992, about 21,000 cases of ovarian cancer were reported, and about 13,000 women died from the disease. [Chapter 321, Ovarian Cancer, *Harrison's Principles of Internal Medicine,* 13th ed., Isselbacher et al., eds., McGraw-Hill, New York (1994), pages 1853–1858; American Cancer Society Statistics, *Cancer J. Clinicians,* 45:30 (1995). Epithelial ovarian cancer, the most common ovarian cancer, has a distinctive pattern of spread: in addition to metastasis through the lymphatic and blood vessels to areas such as the liver, lung and brain, cancer cells may also migrate through the peritoneum to produce multiple metastatic nodules in the visceral and parietal peritoneum and the hemidiaphragms. Early stage ovarian cancer is often asymptomatic and is detected coincidentally by palpating an ovarian mass on pelvic examination. In premenopausal patients, about 95% of these masses are benign. Even after menopause, 70% of masses are benign but detection of any enlargement requires exploratory surgery. In postmenopausal women with a pelvic mass, a markedly elevated serum CA-125 level of greater than 95 U/ml indicates malignancy with a 96% positive predictive value. [Chapter 321, Ovarian Cancer, *Harrison's Principles of Internal Medicine,* supra.]

Epithelial ovarian cancer is seldom encountered in women less than 35 years of age. Its incidence increases sharply with advancing age and peaks at ages 75 to 80, with the median age being 60 years. The single most important risk factor for this cancer is a strong family history of breast or ovarian cancer. In families in which ovarian, breast, endometrial or colon cancer can be tracked as an apparent autosomal dominant trait, the risk of this cancer can be as high as 50%. Having a single first-degree relative with ovarian cancer increases a woman's risk by at least threefold, and having a personal history of breast or colorectal cancer increases the risk of subsequently developing ovarian cancer by two-fold. [Chapter 321, Ovarian Cancer, *Harrison's Principles of Internal Medicine,* supra.] In addition, those with identifiable genetic mutations in genes such as BRCA1 also have an increased risk. Baker et al., Etiology, Biology, and Epidemiology of Ovarian Cancer, *Seminars in Surgical Oncology* 10: 242–248, 1994; Amus et al., Genetic Epidemiology of Epithelial Ovarian Cancer, *Cancer* 71: 566–72, 1993; Whitmore, Characteristics Relating To Ovarian Cancer Risk: Implications for Preventing and Detection, *Gynecologie Oncology* 55, 515–19, 1994. Oncogenes associated with ovarian cancers include the HER-2/neu (c-erbB-2) gene, which is overexpressed in a third of ovarian cancers, the fms oncogene, and abnormalities in the p53 gene, which are seen in about half of ovarian cancers. A number of environmental factors have also been associated with a higher risk of epithelial ovarian cancer, including a high fat diet and intake of lactose in subjects with relatively low tissue levels of galactose-1-phosphate uridyl transferase.

In epidemiological studies, behavior associated with decreased ovulation, such as pregnancy, breastfeeding and use of estrogen-progestin combination oral contraceptive medications, decrease the risk of ovarian cancer; use of estrogen-progestin combination oral contraceptives for as long as 5 years can reduce the risk of ovarian cancer by 50%. Greene et al., The Epidemiology of Ovarian Cancer, *Seminars Oncology,* 11: 209–225, 1984; Whitmore et al., Characteristics Relating To Ovarian Cancer Risk: Collaborative Analysis of 12 US Case-Control Studies, *American J. Epidemiology* 136: 1212–20, 1992. Conversely, early menarche, late menopause and nulliparity (no pregnancies) have been shown to increase the risk of ovarian cancer. The risk has been shown to positively correlate with the number of ovulatory cycles in a woman's lifetime. Wu et al., Personal and Environmental Characteristics Related To Epithelial Ovarian Cancer, *American J. Epidemiology,* Vol. 108(6) 1216–1227. The long-term use of ovulation-inducing ovarian hyperstimulants such as clomiphene has been shown to be associated with an increased risk of ovarian cancer in some women. Rossary et al., Ovarian Tumors in a Cohort Of Infertile Women, *New Engl. J. Med.,* 331: 771–6, 1994. Thus, some factors that favor prolonged and persistent ovulation have been thought to increase ovarian cancer risk, whereas some factors that suppress ovulation have been thought to decrease risk. [Chapter 321, Ovarian Cancer, *Harrison's Principles of Internal Medicine,* supra.] These data have led to the "incessant ovulation" hypothesis for the development of ovarian cancer. Casagrande et al., "Incessant Ovulation" and Ovarian Cancer, *Lancet* at 170–73 (Jul. 28, 1979). This hypothesis is that repeated ovulation cycles, each of which involves the disruption and repair of the ovarian surface epithelium, may cause neoplastic transformation of the ovarian epithelium in susceptible individuals and that the risk of ovarian cancer is associated with the number of ovulation cycles in a woman's lifetime.

There is no established pharmaceutical approach to the prevention of ovarian cancer. For all women, especially those at high risk of developing this disease, the only option available at this time is surgical removal of the ovaries, with all of the attendant risks and subsequent adverse health consequences due to resulting estrogen deficiency.

Although epidemiological evidence suggests that the use of combination oral contraceptives, which contain both an estrogen and a progestin, is associated with a subsequent reduced risk of developing epithelial ovarian cancer, the mechanism for this protective effect is unknown, and oral contraceptive preparations are not currently approved for this purpose. The reduction in risk of ovarian cancer in women who have used estrogen-progestin combination oral contraceptives for at least three years is approximately 40 percent. Moreover, this protective effect increases with the duration of use and persists for up to two decades after discontinuation of use. Rosenberg et al., A Case Control Study of Oral Contraceptive Use and Invasive Epithelial Ovarian Cancer, *The WHO Collaborative Study of Neoplasia and Steroid Contraceptives*; Epithelial Ovarian Cancer and Combined Oral Contraceptives, *Int'l J. Epidemiology* 18: 538–45, 1989; Lee et al., The Reduction in Risk of Ovarian Cancer Associated with Oral Contraceptive Use, *New Engl. J. Med.* 316: 650–51, 1987; Thomas P. Gross, James J. Schlesselman, The Estimated Effect of Oral Contraceptive Use on the Cumulative Risk of Epithelial Ovarian Cancer, *Obstetrics Gynecology* 83: 419–24, 1994; Franceschi et al., Pooled Analysis of 3 European Case-Control Studies of Epithelial Ovarian Cancer: III. Oral Contraceptive Use, *Int'l J. Cancer* 49: 61–65, 1991.

It is commonly believed that the protective effect of oral contraceptives is related to the ability of these drugs to inhibit ovulation. Estrogen-progestin combination oral contraceptives act primarily by suppressing the pituitary gland's production of gonadotropins, thereby inhibiting the hormonal stimulus for ovulation. These combination drugs also have direct inhibitory effects on the reproductive tract, including inducing changes in the cervical mucus that decrease the ability of sperm to enter the uterus, as well as changes in the endometrium that reduce the likelihood of implantation, and reducing fallopian tube motility and uterine secretions.

The epidemiological studies showing the protective effect of combination oral contraceptives evaluated older combination preparations which typically contained higher doses of drug than most contraceptive regimens used today. Common older regimens contained 50 micrograms or more of ethinyl estradiol (an estrogen) or 100 micrograms or more of mestranol (an estrogen) and greater than 1 mg of norethindrone, norethindrone acetate or norethynodrel (a progestin). Table 1 infra lists the progestin and estrogen content of some older regimens. All of the currently used low-dose combination oral contraceptives contain lower doses of both progestin and estrogen, as well as a lower ratio of progestin to estrogen. Consequently, it has not been definitively established that the newer low-dose combination oral contraceptives are associated with the same protective effect as the older high-dose combination contraceptives. Rosenblatt et al., High Dose and Low Dose Combined Oral Contraceptives: Protective Against Epithelial Ovarian Cancer and The Length of the Protective Effect, *Eur. J. Cancer,* 28: 1870–76, 1992.

Despite the overall safety of combination oral contraceptives, their use is not recommended for women smokers older than age 35, for women of all ages who are at increased risk for myocardial infarction, for women with liver disease, and for women older than age 40. Serious and potentially fatal side effects include deep vein thrombosis, pulmonary emboli, myocardial infarction, thromboembolic stroke, hemorrhagic stroke, and high blood pressure. In the 35–39 year old age group, the use of oral contraceptives among women smokers doubles their risk of death. After age 40, the mortality rate even in non-smoker women using oral contraceptives (32.0 per 100,000) is greater than women using no contraception (28.2 per 100,000), while the mortality rate for smoker women is quadrupled (117.6 vs. 28.2 per 100,000). [Chapter 340, Disorders of the Ovary and Female Reproductive Tract, *Harrison's Principles of Internal Medicine*, supra, pages 2017–2036.]

Progestin-only contraceptives do not reliably inhibit ovulation, but are nevertheless contraceptively effective, presumably due to direct effects on the reproductive tract. The actual contraceptive mechanism of action is unclear. Prior epidemiological studies have exhibited no consistent pattern of either increasing or decreasing risk of ovarian cancer according to duration of use. The WHO Collaborative Study of Neoplasia and Steroid Contraceptives Depot-Medroxyprogesterone Acetate(DMPA) and Risk of Epithelial Ovarian Cancer, *Int'l J. Cancer.* 49:191–195 (1991); Liam et al., Risk of Breast, Uterine, Corpus, and Ovarian Cancer in Women Receiving/Medroxyprogesterone Injections, *J. Am. Med. Ass'n* 249:2909–2912 (1983). Thus, unlike the data available for progestin-estrogen combination contraceptives, the prior art relating to progestin-only contraceptives does not suggest that the use of a progestin reduces the risk of epithelial ovarian cancer.

Estrogen, alone or with low doses of progestin, is also used as hormonal replacement therapy in menopausal women. For long term use, Premarin® (conjugated equine estrogen) is generally given at a dose of 0.625 mg orally daily (equivalent to 10 to 20 $\mu$g ethinyl estradiol orally per day) or an equivalent dose transdermally. Other regimens add cyclic progestins or continuous low-dose progestins, typically 2.5 to 10 mg per day of Provera® (medroxyprogesterone acetate). One epidemiologic study has suggested that hormone replacement therapy with estrogen alone may be associated with an increased risk of developing ovarian cancer. Rodriguez et al., Estrogen Replacement Therapy and Fatal Ovarian Cancer, *Am. J. Epidemiology,* 141:828–835 (1995).

SUMMARY OF THE INVENTION

The present invention provides a method for preventing the development of epithelial ovarian cancer by administering progestin products, either alone or in combination with other agents, such as estrogen products. A method is provided of preventing ovarian cancer comprising administering to a female subject an amount of progestin product effective to increase apoptosis in ovarian epithelial cells of the female subject.

It is further the object of this invention to expand the clinical usage of progestin drugs beyond the current use of these drugs as oral contraceptive agents in young women or as part of estrogen-progestin hormone replacement regimens in postmenopausal women. One aspect of the invention provides a method for preventing the development of ovarian cancer comprising administering to a female subject a composition consisting essentially of a progestin product (i.e., a progestin product alone without an estrogen product).

The invention also provides a method for preventing the development of ovarian cancer comprising administering a progestin product to a female subject according to a regimen that is not effective for contraception. This can be accomplished in a number of ways, including altering the dosage of progestin product, the type of progestin product, the ratio of progestin product to estrogen product, or the timing of administration.

With regard to infertile female subjects, the present invention further provides a method for preventing the development of ovarian cancer comprising administering a progestin product according to a regimen that is different from that currently used for hormone replacement therapy. Again, this can be accomplished in a number of ways, including altering the dosage, timing, ratio of progestin product to estrogen product, or the type of progestin product.

It is contemplated that the progestin product may be concurrently administered in combination with additional agent(s), such as an estrogen product, a second progestin product, an androgenic agent, an androgen agonist, a progestin agonist, an estrogen antagonist, or another hormone product, or with other agents that induce apoptosis of ovarian epithelial cells. Such additional agent(s) may be selected to improve the activity of the progestin agent for preventing ovarian cancer or to reduce any side effects of the progestin agent. Preferably if estrogen is used as the second agent, it is used in doses lower than those currently used in combination oral contraceptive regimens or in doses selected to provide a progestin/estrogen product ratio that is higher than the ratio currently used in combination oral contraceptives.

The present invention is based on the discovery that administration of progestin alone induced an accelerated rate of apoptosis in vivo in ovarian epithelial cells of monkeys. Apoptosis is one of the most important mechanisms used for the elimination of cells that have sustained DNA damage and which are thus prone to transformation into malignant neoplasms. This novel explanation for the association between estrogen-progestin combination oral contraceptive use and a reduced risk of ovarian cancer is a complete departure from the widely accepted theory that suppression of "incessant ovulation" is responsible for this reduced risk. This finding thus relates to the discovery that progestin alone or estrogen-progestin combinations may be administered in ways that do not effectively inhibit ovulation or otherwise inhibit contraception, yet which still prevent ovarian cancer.

The invention further relates to the discovery that progestin alone induced a greater rate of apoptosis than a combination of estrogen and progestin, which in turn induced a greater rate of apoptosis than estrogen alone. The invention thus contemplates that administration of progestin alone be effective for preventing the development of ovarian cancer, contrary to the suggestions of the prior art that progestin has no effect on risk of ovarian cancer.

DETAILED DESCRIPTION OF THE INVENTION

The present invention generally relates to methods for preventing the development of epithelial ovarian cancer by administering a progestin product, either alone or in combination with other agents, such as an estrogen product. The invention provides a method of preventing ovarian cancer comprising administering to a female subject an amount of progestin product effective to increase apoptosis in ovarian epithelial cells of the female subject. The invention also provides a method of increasing apoptosis in ovarian epithelial cells of a female subject comprising administering to a female subject an amount of progestin product effective to increase apoptosis in ovarian epithelial cells of the female subject. In particular, the methods of the present invention will be particularly advantageous when applied to females at high risk of developing ovarian cancer.

In a second aspect of the invention, a method is provided for preventing the development of ovarian cancer comprising administering to a female subject a composition consisting essentially of a progestin product (i.e., a progestin product alone without an estrogen product). The female subject may be a fertile female or an infertile female, including perimenopausal and postmenopausal women. The most preferred product for administration would be an agent that provides the greatest rate of apoptosis of ovarian epithelial cells with the least side effects. Use of a progestin product for longer durations, or at higher doses, at appropriate intervals, and/or use of an agent that maximizes apoptosis, without creating unacceptable side effects, in fertile or infertile women may reduce the risk of ovarian cancer further than that previously achieved by combination oral contraceptive use, potentially by as much as 60% to 80%.

The invention further contemplates expanding the clinical usage of progestin drugs beyond the current use of these drugs as oral contraceptive agents in young women or as part of estrogen-progestin hormone replacement regimens in postmenopausal women. Specifically, a third aspect of the present invention provides a method for preventing the development of ovarian cancer comprising administering a progestin product to a fertile female subject according to a regimen that is not effective for contraception. This can be accomplished in a number of ways, including altering the dosage of progestin product, the type of progestin product, the ratio of progestin product to estrogen product, or the timing of administration. Also specifically contemplated is administration of a progestin product in doses higher than those currently used for contraception.

Oral contraceptive administration regimens are selected to simulate the normal menstrual cycle, which averages 28 days in women of reproductive age. The menstrual cycle begins at the onset of a menstrual bleeding episode and lasts until the onset of the next. Thus, day 1 of a cycle would be the first day of menstruation, and day 28 would be the day before the onset of the next menstrual bleeding episode. Oral contraceptives are typically taken daily, at the same time each day, for 21 days, followed by a placebo for the next 7 days. The female generally experiences a menstrual bleeding episode during the seven-day placebo period. Thus, a woman first starting on oral contraceptives is generally instructed to begin taking them at some time between day 1 and 7.

The oral contraceptives must be taken according to the daily regimen for a full menstrual cycle before they are effective for contraception. A woman beginning an oral contraceptive regimen is not effectively protected against conception if the oral contraceptives are taken for less than the full menstrual cycle, if they are not taken daily, and if they are not taken for 21 consecutive days. A minimum blood level of the exogenously administered estrogen or progestin hormones must be maintained daily in order to suppress ovulation. If the blood level drops too low, ovulation may occur and the other inhibitory mechanisms on the reproductive tract may fail to prevent conception.

Thus, according to this third aspect of present invention, a regimen of progestin product administration that is not effective for contraception would include, for example, administering or delivering (regardless of whether the route of administration is oral or via injection or implant) progestin product in doses lower than those effective for contraceptive use and/or lower than those previously used in contraceptives; administering progestin product with estrogen product at a progestin/estrogen ratio that is higher than that previously used in contraceptives; administering the drug for less than one menstrual cycle; administering the drug for nonconsecutive menstrual cycles, e.g., every other cycle; administering the drug for one or more menstrual cycles for fewer than 21 consecutive days in each cycle; delivering the drug (regardless of whether the route of administration is oral or via injection or implant) with a less than daily frequency; or administering the drug for one or more menstrual cycles according to a regimen that fails to maintain a contraceptive blood level of the drug or its active metabolite for 21 consecutive days in each cycle. A regimen of progestin product administration that is different from that currently used for contraception would also include administering the progestin product at a daily dose higher than that currently used for contraception.

Exemplary regimens according to this third aspect of the invention include administering progestin product at a dose less than a dose equivalent to 1 mg daily of norethindrone, more preferably less than 0.2 mg daily, or less than 0.05 mg daily, and possibly as low as 0.025 mg daily of a norethindrone equivalent dose. Another exemplary regimen includes administering progestin product at a dose higher than 10 mg daily of a norethindrone equivalent dose. A further exemplary regimen includes administering a progestin product with an estrogen product at a ratio of greater than 239:1 by weight in norethindrone/ethinyl estradiol equivalent doses. Additional exemplary regimens include administering any dose of progestin product with a less than daily frequency; or administering any dose of progestin product for a brief time, e.g., one week only, during the menstrual cycle. It is contemplated that the most desirable mode of administration may be administering the progestin product for a brief period sufficient to produce apoptotic turnover of damaged ovarian cells, followed by repeated dosing periods at intervals, for example 1, 3, 5 or 10 years, selected to provide apoptotic turnover adequate to prevent malignant transformations. The most preferable progestin product for administration would be a product that maximizes the apoptotic turnover of ovarian epithelial cells and minimizes any side effects.

The fourth aspect of the present invention provides a method for preventing the development of ovarian cancer in infertile female subjects, comprising administering a progestin product according to a regimen that is different from that currently used for hormone replacement therapy. Again, this can be accomplished in a number of ways, including altering the dosage, timing, ratio of progestin product to estrogen product, or the type of progestin product. Other contemplated regimens would include, for example, administering or delivering progestin product in doses lower or higher than those previously used in hormone replacement therapy; or administering progestin product with estrogen product at a progestin/estrogen ratio that is higher than that previously used in hormone replacement therapy.

Estrogen is the primary agent in hormone replacement therapy. Postmenopausal women are generally given estrogen alone, or with low doses of progestins. The hormones may be administered continuously or cyclically. Continuous administration is typically 0.625 mg Premarin® (a conjugated equine estrogen) daily or its equivalent, with 2.5 mg Provera® (medroxyprogesterone acetate) daily. Cyclical administration is typically 25 consecutive days of 0.625 mg Premarin® daily, with 10 mg Provera® daily on days 16 through 25, followed by 5 days of no hormone treatment (during which time these women will menstruate).

Exemplary regimens according to the fourth aspect of the present invention include doses of progestin product less than a dose equivalent to 2.5 mg of medroxyprogesterone acetate daily (equivalent to about 1.25 mg of norethindrone), or less than 0.5 mg daily of a norethindrone equivalent dose. Another exemplary regimen includes a dose of progestin product greater than a dose equivalent to 10 mg of medroxyprogesterone acetate daily (equivalent to about 5 mg of norethindrone) for 10 days every month. A further exemplary regimen includes doses of progestin product with estrogen product at a ratio of greater than 1:1 by weight in norethindrone/ethinyl estradiol equivalent doses, or a ratio of greater than 50:1 or 100:1. It is also contemplated that the most desirable mode of administration may be administering the progestin product for a brief period sufficient to produce apoptotic turnover followed by repeated dosing periods at selected intervals adequate to prevent malignant transformations. A presently preferred progestin product is levonorgestrel or other 19-nortestosterone derivatives. The most preferable progestin product for administration would be a product that maximizes the apoptotic turnover of ovarian epithelial cells and minimizes any side effects.

The present invention yet further provides a novel use of progestin product in preparation of a non-contraceptive medicament for prevention of ovarian cancer in female subjects, as well as a novel use of progestin product in preparation of a medicament for prevention of ovarian cancer in infertile female subjects.

All doses given herein are appropriate for a female subject of about 60 kg weight; the dosages naturally will vary more or less depending on the weight of the subject. The doses may be increased or decreased, and the duration of treatment may be shortened or lengthened as determined by the treating physician. The frequency of dosing will depend on the pharmacokinetic parameters of the agents and the route of administration. The optimal pharmaceutical formulation will be determined by one skilled in the art depending upon the route of administration and desired dosage. See for example, Remington's Pharmaceutical Sciences, 18th Ed. (1990, Mack Publishing Co., Easton, Pa. 18042) pages 1435–1712, the disclosure of which is hereby incorporated by reference. Such formulations may influence the physical state, stability, rate of in vivo release, and rate of in vivo clearance of the administered agents.

Those of ordinary skill in the art will readily optimize effective dosages and concurrent administration regimens as determined by good medical practice and the clinical condition of the individual patient. Regardless of the manner of administration, the specific dose may be calculated according to body weight, body surface area or organ size. Further refinement of the calculations necessary to determine the appropriate dosage for treatment involving each of the above mentioned formulations is routinely made by those of ordinary skill in the art and is within the ambit of tasks routinely performed by them without undue experimentation, especially in light of the dosage information and assays disclosed herein. Appropriate dosages may be ascertained through use of established assays for determining dosages in conjunction with appropriate dose-response data. The final dosage regimen will be determined by the attending physician, considering various factors which modify the action of drugs, e.g. the drug's specific activity, the severity of the damage and the responsiveness of the patient, the age, condition, body weight, sex and diet of the patient, the severity of any infection, time of administration and other clinical factors. As studies are conducted, further information will emerge regarding the appropriate dosage levels for the treatment of various diseases and conditions.

It is contemplated that the routes of delivery of progestin products (either alone or in combination with other pharmaceuticals) could include oral, sublingual, injectable (including short-acting, depot, implant and pellet forms injected subcutaneously or intramuscularly), vaginal creams, suppositories, pessaries, rings, rectal suppositories, intrauterine devices, and transdermal forms such as patches and creams.

The present invention is related to the discovery that administration of progestin alone induced an accelerated rate of apoptosis in vivo in ovarian epithelial cells of monkeys. Apoptosis is a process whereby a genetic program within the cell is activated to trigger a specific series of events within the cell eventually leading to the death and efficient disposal of the cell. Richard Lockshin, Zahra Zakeri, *The Biology of Cell Death and Its Relationship to Aging in Cellular Aging and Cell Death*, pp. 167–180, 1996. Wiley-Liss Inc., Editors: N. J. Holbrook, G. Martin, R. Lockshin. C. Miligan, L. Schwartz, *Programmed Cell Death During Development of Animals in Cellular Aging and Cell Death*, pp. 181–208, 1996. Wiley-Liss Inc. P53-*Dependent Apoptosis in Tumor Progression and in Cancer Therapy*, Scott W. Lowe, H. Earl Ruley in *Cellular Aging and Cell Death*, pp. 209–234, 1996. Wiley-Liss, Inc.

For cells that have sustained DNA damage, apoptosis is one of the most important mechanisms used for the elimination of these cells, the preservation of which could otherwise lead to the development of malignant neoplasms. Canman et al., DNA Damage Responses. P-53 Induction, Cell Cycle Pertubations, and Apoptosis, *Cold Spring Harbor Symp. Ouant. Biol.,* 59:277–286 (1994). Thus, the apoptosis pathway is a virtually universal safeguard to prevent the persistence and proliferation of damaged cells that can be lethal to the organism. For normal tissues, the processes of cell proliferation and cell death are usually in a steady-state balance, and the apoptosis mechanism not only serves to prevent overgrowth of tissue, but also to eliminate those cells that are aberrant and therefore prone to resist normal growth regulatory controls.

An accelerated rate of apoptosis would facilitate the destruction and thereby removal of ovarian surface epithelial cells which have defective DNA and which have the potential to transform into malignant neoplasms. Given the importance of the apoptotic pathway for removal of abnormal cells from tissues, and thus the protection of normal tissues from neoplastic transformation, it is likely that the induction of apoptosis by progestins is one of the major (if not the major) mechanism underlying the effect of combination oral contraceptives in reducing the risk of ovarian cancer.

This novel explanation for the association between estrogen-progestin combination oral contraceptive use and a reduced risk of ovarian cancer is a complete departure from the widely accepted theory that suppression of "incessant ovulation" is responsible for this reduced risk. This finding thus leads to the discovery that progestin alone or estrogen-progestin combinations may be administered in ways that do not effectively inhibit ovulation or otherwise inhibit contraception, yet which still prevent ovarian cancer. Since the protective mechanism for progestin containing compounds is related to a direct biological effect on the ovarian epithelium, it is likely that the use of progestin drugs in postmenopausal women who are not ovulating will also be protective against the development of epithelial ovarian carcinoma.

The invention is further based on the discovery that use of progestin alone induces a more accelerated rate of apoptosis in vivo in ovarian epithelial cells of monkeys compared to the combination of estrogen and progestin, which in turn induced a greater rate of apoptosis than estrogen alone. The implications of this discovery are that the progestin component of the oral contraceptive is responsible for this effect, and that administration of progestin alone may be effective for preventing the development of ovarian cancer, contrary to established reports that it has no effect on risk of ovarian cancer. Since the human-equivalent dose of the progestin only dose given the monkeys is insufficient to reliably block ovulation in women, yet showed the greatest degree of apoptosis (and thus protection), this indicates that ovulatory blockade per se is not essential for the protective effect, and that progestin product only (or with estrogen product) in doses less than sufficient to prevent ovulation is effective in preventing ovarian cancer.

The term "progestin product" or "progestogenic agent" as used herein includes any drug which binds to the progestin receptor and induces a progestational effect. This definition thus includes all of the known progestins, derivatives of progesterone or testosterone that have progestin activity, progestin agonists, and any other agent that increases the rate of apoptosis in ovarian epithelial cells. It is contemplated that not only presently available progestins but also progestins introduced in the future will be useful according to the present invention. The known synthetic progestins are mainly derivatives of 17-alpha-hydroxy-progesterone or 19-nortestosterone. These progestins can be classified into three groups: the pregnane, estrane, and gonane derivatives. The pregnane progestins, derived from 17 alphahydroxyprogesterone, include, for example, medroxyprogesterone acetate, chlormadinone acetate, megestrol acetate, and cyproterone acetate. All of these are roughly 20% to 50% of the potency of norethindrone. The estranes, derived from 19-nortestosterone include norethindrone, norethynodrel, lynestrenol, norethindrone acetate, ethynodiol acetate, and norethindrone enanthate. All of these are metabolized to norethindrone and are roughly equivalent to the same dosage of norethindrone. The gonanes are derived from the basic estrane structure, with the addition of an ethyl group of position 13 of the molecule. This additional ethyl group confers augmented progestogenic activity, and also significant androgenic effects. Drugs in this group include, for example, norgestrel (-d and -1), norgestimate, desogestrel, and gestodene. All of these are roughly equivalent to four times the dose of norethindrone. The oral preparations currently on the market are: norgestrel 0.075 mg, medroxyprogesterone acetate 2.5 mg, 5.0 mg, and 10.0 mg, norethindrone 0.35 mg, and norethindrone acetate 0.50 mg.

Progestogenic agents have a variety of biological effects including antifertility, inhibition of midcycle luteinizing hormone surge, inhibition of ovulation, inhibition of corpus luteium function and development, and production of a secretory endometrium. In addition, the progestins have important effects on carbohydrate metabolism, lipid and lipoprotein metabolism and have cardiovascular effects.

Progestogenic potency can be measured by other biological outcomes, including the ability of these agents to bind to the progesterone receptor. The progestogenic activity of the various progestin derivatives can vary. In a review of the literature, Dorflinger has noted that the progestogenic potency of all these estrane drugs is equivalent, and exhibit only 5–10 percent of the progestogenic activity of levonorgestrel.

In addition to their progestogenic effects, the synthetic progestins have the ability to bind to both estrogen and androgen receptors, to a varying degree. These drugs can therefore have estrogenic, androgenic, antiestrogenic or antiandrogenic effects. For example, the estrane progestins are weak estrogen agonists, and therefor have slight estrogen activity. In contrast, the gonane levonorgestrel has no estrogenic activity, but does have androgenic activity. The 19-nortestosterone derivatives have androgenic activity mediated by variable binding to the androgen receptor.

Given the diverse binding patterns of the different synthetic progestins to various receptors (progestin, androgen and estrogen receptors), the estrogenic, progestogenic and androgenic activity can vary among the different synthetic progestin formulations, thus leading to varying degrees of progestational activity and androgenic side effects. For example, the progestational binding activity of norethindrone is less than 20% that of levonorgestrel and less than 10% that of 3-ketodesogestrel, the active metabolite of the progestin desogestrel, while the binding affinity of norethindrone to the androgen receptor is similar to that of 3-ketodesogestrel, and yet both compounds have less than 50% of the nuclear cell androgenic activity of levonorgestrel.

It is contemplated that the progestins with more androgenic activity and less estrogenic activity, such as levonorgestrel, may be preferred as more potent for preventing the development of ovarian cancer. Such agents would include the 19-nortestosterone derivatives, such as norethindrone, norethynodrel, lynestrenol, norethindrone acetate, ethynodiol acetate, and norethindrone enanthate.

The term "estrogen product" as used herein includes ethinyl estradiol, mestranol (a 50 mg dosage of which is equivalent to 35 mg of ethinyl estradiol), conjugated equine estrogen, estrone, estradiol, esterified estrogens, estropipate, and other estrogen equivalents and estrogen agonists.

"Concurrent administration" or "co-administration" as used herein includes administration of the agents together, or before or after each other. The agents may be administered by different routes. For example, one agent may be administered intravenously while the second agent is administered intramuscularly, intravenously or orally. They may be administered simultaneously or sequentially, as long as they are given in a manner sufficient to allow both agents to achieve effective concentrations in the body.

The term "infertile female" as used herein includes perimenopausal and postmenopausal females past the age of reproduction and younger women not capable of conception, including ovulation, fertilization and implantation.

The term "effective for contraception" as used herein includes sufficient inhibition of fertility, including ovulation or implantation.

The term "contraceptive blood level" as used herein includes a blood level sufficient to inhibit fertility, including ovulation or implantation.

The term "females at high risk of developing ovarian cancer" includes females with a family history of breast or ovarian cancer, females with a prior history of breast or ovarian cancer, or females with a mutation in the BRCA1 gene or any other mutation shown to be associated with a high risk of developing ovarian cancer.

Various combinations of progestin and estrogen that have been used in oral contraceptives are shown in Table 1.

become more important over time. Second, with this downward trend in dosage, it is apparent that the relative ratio of progestin to estrogen is also trending downward. By contrast, the present invention emphasizes the greater importance of progestin in combination with estrogen, and thus emphasizes combination ratios even higher than those ratios, e.g., 100-1, that have long since been abandoned.

Other aspects and advantages of the present invention will be understood upon consideration of the following illustrative examples. Example 1 addresses the effect of administration of progestin or estrogen products, alone or in combination, on the ovarian epithelial cells of monkeys. Example 2 addresses the effect of progestin and estrogen products, alone or in combination, on the ovaries of humans. Example 3 addresses the effect of hormonally active agents, alone or in combination, in vitro on human ovarian tissue. Example 4 addresses the effect of gonadal hypertrophy on rodent ovaries. Example 5 addresses the effect of various hormonally active products, alone or in combination, on monkey ovaries. Example 6 addresses the effect of various hormonally active agents on the ovarian tissue of transgenic mice that have been altered to have altered expression of receptors, growth factors, integrins or protooncogenes.

EXAMPLE 1

Effect of Estrogen and Progestin in vivo on Monkey Ovaries

Young female adult cynomolgus monkeys were fed a diet for two years that contained either no hormones, the oral

TABLE 1

Previously Used Combinations of Progestin and Estrogen

| Progestin | Dose (mg) | Norethindrone Equivalent Dose | Estrogen | Dose (mg) | EE Equivalent Dose (mg) | P/E Ratio |
|---|---|---|---|---|---|---|
| Norethynodrel | 9.85 | 9.85 | Mestranol | 0.150 | 0.105 | 93.810 |
|  | 5.00 | 5.00 |  | 0.075 | 0.053 | 95.238 |
|  | 2.50 | 2.50 |  | 0.036 | 0.025 | 99.206 |
|  | 2.50 | 2.50 |  | 0.100 | 0.070 | 35.714 |
| Norethindrone | 10.00 | 10.00 | Mestranol | 0.060 | 0.042 | 238.095 |
|  | 2.00 | 2.00 |  | 0.100 | 0.070 | 28.571 |
|  | 1.00 | 1.00 |  | 0.050 | 0.035 | 28.571 |
|  | 1.00 | 1.00 |  | 0.080 | 0.056 | 17.857 |
| Norethindrone | 1.00 | 1.00 | Ethinyl | 0.050 | 0.050 | 20.000 |
|  | 0.50 | 0.50 | estradiol | 0.035 | 0.035 | 14.286 |
|  | 0.40 | 0.40 |  | 0.035 | 0.035 | 11.429 |
| Norethindrone acetate | 2.50 | 2.50 | EE | 0.050 | 0.050 | 50.000 |
|  | 1.00 | 1.00 |  | 0.050 | 0.050 | 20.000 |
|  | 0.60 | 0.60 |  | 0.030 | 0.030 | 20.000 |
|  | 1.50 | 1.50 |  | 0.030 | 0.030 | 50.000 |
|  | 1.00 | 1.00 |  | 0.020 | 0.020 | 50.000 |
| Ethynodiol diacetate | 1.00 | 1.00 | Mestranol | 0.100 | 0.070 | 14.286 |
| Ethynodiol diacetate | 1.00 | 1.00 | EE | 0.050 | 0.050 | 20.000 |
| dl-Norgestrel | 0.50 | 2.00 | EE | 0.050 | 0.050 | 10.000 |
|  | 0.30 | 1.20 |  | 0.030 | 0.030 | 10.000 |

Equivalencies
50 mg Mestranol 35 mg Ethinyl estradiol (EE)
0.5 mg dl-Norgestrel = 2 mg Norethindrone Each block describes a specific combination of progestin and estrogen, e.g., norethynodrel and mestranol, and within each block older combinations are listed first, with successively newer combinations following. Two trends are evident. First, over time the size and ratio of the dosages has decreased, i.e., the downward trend of the progestin component is steeper than the downward trend of the estrogen component. On a relative scale, therefore, estrogen has combination contraceptive "Triphasil®," the estrogenic component of "Triphasil®" (ethinyl estradiol) alone, or the progestin component of "Triphasil®" (levonorgestrel) alone, each administered in the same pattern that occurs in a "Triphasil®" regimen. Doses were scaled on the basis of caloric intake, which is the accepted way to achieve human-equivalent doses. The human-equivalent doses were thus: six days of 0.030 mg ethinyl estradiol+0.050 mg levonorgestrel, followed by 5 days of 0.040 mg ethinyl estradiol+0.075 mg levonorgestrel, followed by 10 days of 0.030 mg ethinyl estradiol+0.125 mg levonorgestrel, followed by 7 days of no treatment. This cyclic regimen was repeated every 28 days continuously for 2 years.

At the completion of the two years of the study, the animals were sacrificed, and their ovaries were removed and both formalin fixed and paraffin embedded as well as flash frozen and stored at minus 70 degrees Celsius. Five-micron ovarian sections were mounted on coated slides, and stained with the Apoptag-plus kit (Oncor, Gaithersburg, Md.), which specifically labels the 3' end of free DNA fragments in cells undergoing DNA fragmentation, a characteristic of apoptosis. After staining, cells undergoing apoptosis were easily identified by their dark brown nuclear discoloration. The ovarian surface epithelium was examined histologically to assess ovarian epithelial morphology and to determine the percentage of ovarian cells undergoing apoptosis. To calculate the percentage of ovarian epithelial cells undergoing apoptosis, both the total number of ovarian epithelial cells and the number undergoing apoptosis were counted on each five-micron ovarian section. At each step, the investigators were completely blinded with regard to which treatment group was associated with each ovary.

The ovarian surface epithelium is comprised of a single layer of epithelial cells that rests on a basement membrane overlying the ovarian cortex. In the control and non-progestin treated monkeys, the ovarian surface epithelium typically had a lush appearance with the epithelial cells containing abundant cytoplasm and visible microvilli at the surface with apoptotic cells rarely seen. In the progestin treated monkeys, the ovarian surface epithelium was observed to contain numerous brown-staining apoptotic cells.

The median percentage of ovarian epithelial cells undergoing apoptosis for each of the treatment groups is shown below in Table 2.

TABLE 2

Apoptotic Effect of Four Treatments On Monkey Epithelia

| Treatment | Number | Median Percent of Apoptotic Cell Counts | Range of Percent of Apoptotic Cell Counts |
| --- | --- | --- | --- |
| Control | 20 | 3.8% | 0.1–33.0% |
| Ethinyl-estriadol-only | 20 | 1.8% | 0.1–28.6% |
| Combination Pill | 17 | 14.5% | 3.0–61.0% |
| Levonorgestrel | 18 | 24.9% | 3.5–61.8% |

Multiple Comparisons: Control - Levonorgestrel ($p < 0.001$)
Combination Pill - Ethinyl-estradiol ($p < 0.001$)
Ethinyl-estradiol - Levonorgestrel ($p < 0.001$)
Control - Combination Pill ($p < 0.05$)

From Table 2, the median percentage of apoptosis in the control group of monkeys not receiving any hormonal therapy was approximately 3.8%. Statistically, this was not significantly different from the rate of apoptosis seen in the ovarian epithelium in monkeys receiving only the estrogen component of "Triphasil®," ethinyl estradiol, in which the median percentage of apoptosis was 1.8%.

A marked and significantly greater level of apoptosis was noted in the other two groups of monkeys—those that received the combination pill (containing both ethinyl estradiol and levonorgestrel) and those that received levonorgestrel (the progestin) alone. In this latter group (progestin alone), the observed median percentage of cells undergoing apoptosis was over six times greater than the level of apoptosis observed in the control, untreated monkeys. Because the only difference between the combination pill group and estrogen-alone group is the presence of the levonorgestrel component of the combination pill, and because the degree of apoptosis of the ovarian epithelium in the estrogen-alone group was no different than that of the control group, these data demonstrate that the accelerated rate of apoptosis in the ovarian epithelium in combination pill treated monkeys is due to the effects of the progestational component (levonorgestrel) of the combination pill. Moreover, the higher rate of apoptosis among the monkeys that received a progestational agent alone than in the monkeys that received the combination pill, although not statistically significant, indicates that progestin-only treatment is more effective at inducing apoptosis of the ovarian surface epithelium than a progestin/estrogen combination treatment.

EXAMPLE 2

Effect of Progestin and Estrogen in vivo on Human Ovaries

Various progestins alone, including pregnanes, estranes and gonanes, various estrogens alone, or various progestin-estrogen combinations at varying doses are administered to women for at least one month prior to a scheduled surgery for removal of the ovaries and uterus. In particular,. regimens of estrogen alone, estrogen with medroxyprogesterone acetate (or another 17-hydroxy-progesterone derivative), and estrogen with levonorgestrel (or another 19-nortestosterone derivative) are evaluated. To evaluate the effects of the different dosage regimens, the ovaries are examined for various markers, including apoptosis, proliferation, expression of growth factors, expression of steroid hormone receptors, and expression of other enzymes or genes.

EXAMPLE 3

Effect of Hormonally Active Agents in vitro on Human Ovarian Tissue

Ovarian epithelia cultured from ovaries removed from normal women or women with epithelial ovarian cancer are treated with various progestins alone, including pregnanes, estranes and gonanes, various estrogens alone, various progestin-estrogen combinations, progesterone receptor agonists, progesterone receptor antagonists, estrogen receptor agonists, or estrogen receptor antagonists, each at varying doses and varying durations, from e.g., 24 hours to 7 days. The ovarian tissue is then examined for various markers, including apoptosis, proliferation, expression of growth factors, expression of steroid hormone receptors, and expression of other enzymes or genes. The most potent agent for inducing apoptosis is determined.

EXAMPLE 4

Effect of Gonadal Hypertrophy on Rodent Ovaries

The ovaries of mice or rats are modestly "hyperstimulated" by compensatory gonadal hypertrophy after unilateral oophorectomy. The ovaries of the control animals, which received no treatment, are removed and examined at age 4, 4.5, 5 and 6 months. One ovary of the test animals is removed and examined at age 4 months, and the remaining ovary of each test animal is removed and examined at either age 4.5, 5 or 6 months. The ovarian tissue is examined for various markers, including apoptosis, proliferation, expression of growth factors, expression of steroid hormone receptors, and expression of other enzymes or genes.

EXAMPLE 5

Effect of Hormonally Active Agents in vivo on Monkey Ovaries

Mature young female monkeys are treated with one of the following: control, leuprolide acetate (a gonadotropin releasing hormone [GnRH or LHRH] agonist), various oral contraceptives, levonorgestrel, norethindrone, medroxyprogesterone acetate, ethinyl estradiol, testosterone, testosterone derivatives, RU-486, progestin agonists, progestin antagonists, estrogen agonists and estrogen antagonists, each at varying doses. The ovarian tissue is removed and examined for various markers, including apoptosis, proliferation, expression of growth factors, expression of steroid hormone receptors, and expression of other enzymes or genes.

EXAMPLE 6

Effect of Hormonally Active Agents in vivo on Ovaries of Transgenic Mice

The effect of various progestins, estrogens or androgens, each at varying doses, is evaluated on the ovarian tissue of transgenic mice that have been altered to "knockout" their progestin receptor, to have an altered expression of the estrogen receptor, to express BRCA1, or to have altered expression of growth factors, integrins or protooncogenes.

Numerous modifications and variations in the practice of the invention are expected to occur to those skilled in the art upon consideration of the foregoing description on the presently preferred embodiments thereof. Consequently the only limitations which should be placed upon the scope of the present invention are those that appear in the appended claims.

What is claimed are:

1. A method for reducing the risk of ovarian cancer in a post-menopausal female subject in need thereof who is no longer ovulating comprising administering to the post-menopausal female subject a progestin product sensitive to reducing the risk of ovarian cancer in an amount effective to inhibit the conversion of non-normal, non-neoplastic ovarian epithelial cells of the female subject to neoplastic cells.

2. The method of claim 1 wherein said progestin product is a gonane derivative.

3. The method of claim 1 wherein said progestin product is levonorgestrel.

4. A method for reducing the risk of ovarian cancer in a post-menopausal female subject in need thereof who is no longer ovulating comprising administering to the post-menopausal female subject a progestin product sensitive to preventing ovarian cancer in an amount effective to inhibit the conversion of non-normal, non-neoplastic ovarian epithelial cells of the female subject to neoplastic cells.

5. The method of claim 4 wherein said progestin product is a gonane derivative.

6. A method for reducing the risk of ovarian cancer comprising administering a pharmaceutical composition to a post-menopausal female subject in need thereof who is no longer ovulating, said composition comprising a progestin product sensitive to reducing the risk of ovarian cancer in an amount effective to inhibit the conversion of non-normal, non-neoplastic ovarian cells to neoplastic cells.

7. The method of claim 6 wherein said progestin product is a gonane derivative.

8. The combination of claim 6 wherein said progestin product is levonorgestrel.

9. A method for reducing the risk of ovarian cancer comprising administering a pharmaceutical composition to a female subject in need thereof who is no longer ovulating, said composition comprising a progestin product sensitive to reducing the risk of ovarian cancer in an amount effective to increase apoptosis in non-normal ovarian epithelial cells of the female subject.

10. The method of claim 9 wherein said progestin product is a gonane derivative.

11. The method of claim 9 wherein said progestin product is levonorgestrel.

* * * * *